United States Patent
Endo et al.

(10) Patent No.: US 7,134,998 B2
(45) Date of Patent: Nov. 14, 2006

(54) TEAR SECRETION QUANTITY EXAMINATION SYSTEM

(75) Inventors: Koji Endo, Tochigi (JP); Kazuo Tsubota, Chiba (JP); Eiki Goto, Chiba (JP)

(73) Assignee: Kao Corporation, Tokyo (JP)

( * ) Notice: Subject to any disclaimer, the term of this patent is extended or adjusted under 35 U.S.C. 154(b) by 492 days.

(21) Appl. No.: 10/770,443

(22) Filed: Feb. 4, 2004

(65) Prior Publication Data
US 2004/0225204 A1 Nov. 11, 2004

(30) Foreign Application Priority Data
Feb. 10, 2003 (JP) ............................. 2003-032898
Feb. 10, 2003 (JP) ............................. 2003-032899

(51) Int. Cl.
*A61B 5/00* (2006.01)
(52) U.S. Cl. ...................... 600/307; 600/300
(58) Field of Classification Search ............ None
See application file for complete search history.

(56) References Cited

U.S. PATENT DOCUMENTS 4,461,303 A * 7/1984 Refojo et al. ............... 600/307

6,210,000 B1 * 4/2001 Yee ............................. 351/83

FOREIGN PATENT DOCUMENTS

JP 2001-46339 2/2001

OTHER PUBLICATIONS

Masakazu Yamada, et al., "Diagnosis and Treatment of Dry Eye Syndrome from the Standpoint of Tear Evaporation", Journal of the Eye, vol. 7, No. 3, Mar. 30, 1990, pp. 365-370, and p. 476.

* cited by examiner

Primary Examiner—Robert L. Nasser
(74) Attorney, Agent, or Firm—Oblon, Spivak, McClelland, Maier & Neustadt, P.C.

(57) ABSTRACT

A tear secretion quantity examination system for evaluating simply and non-invasively the tear secretion quantity has: a moisture evaporation quantity detection unit for detecting the moisture evaporation quantity from a subject's eye with a humidity sensor; and an operation unit for computing evaluation parameters of the tear secretion quantity based on a detection signal of the moisture evaporation quantity detection unit. The operation means approximates an attenuation portion of saw-tooth responses appearing for each blink in a tear evaporation profile in which the detection value obtained with the humidity sensor is plotted against the time.

9 Claims, 7 Drawing Sheets

TEAR SECRETION QUANTITY EXAMINATION SYSTEM

BACKGROUND OF THE INVENTION

1. Field of the Invention

The present invention relates to a tear secretion quantity examination system suitable for dry-eye evaluation.

2. Description of the Related Art

Tears are secreted by a lacrimal gland situated above the ear side of the eye, form a tear layer on the cornea surface each time the eye blinks, and are discarded to the lacrimal points located at the nasal side. The tears prevent eyes from drying, sterilize and wash them, and supply nutrients thereto; they are indispensable for normal functioning of the eyes. The quantity of tears present on the eye surface is apparently determined by the balance of (1) secretion by the lacrimal gland, (2) discharge from the lacrimal points, and (3) evaporation from the eye surface. When tear secretion is too small, a dry eye condition which is called an ATD (Aqueous Tear Deficiency) is realized.

The tear secretion quantity have been conventionally evaluated by a Schirmer test in which a filtration paper was inserted between the eye and the eyelid and the wetting degree of the filtration paper was studied after 5 minutes, and the tear discharge quantity was evaluated by a clearance test in which fluorescent eye drops are dropped into the eye and the fluorescence yield of the fluorescent eye drops was observed over time. There is no established method for evaluating the tear evaporation quantity, but a method is known which uses a moisture evaporation quantity measurement unit equipped with a quarts oscillator humidity sensor in a tubular body surrounding the eye (Japanese Patent Application Laid-open No. 2001-46339).

However, the problem associated with the Schirmer test was that a filtration paper had to be inserted between the eye and the eyelid, which placed a large burden on the patient.

In the clearance test, fluorescent eye drops are dropped in the eye and after a certain time, the attenuation ratio of fluorescence was studied by using a Schirmer test paper. Therefore, a large burden was placed on the patient, similarly to the Schirmer test. Furthermore, a large fluorescence analyzer and significant space are required for measuring the fluorescence yield.

In the method using the moisture evaporation quantity measurement unit (Japanese Patent Application Laid-open No. 2001-46339), the tear evaporation quantity can be measured in a simple and non-invasive manner, and the amount of information that is obtained with respect to the tear secretion quantity or retention quantity is small.

SUMMARY OF THE INVENTION

Accordingly, an object of the present invention is to provide a method for simple and non-invasive evaluation of the tear secretion quantity or retention quantity.

The inventors have obtained tear evaporation profile by plotting against the time a detection signal which is detected with a humidity sensor in a moisture evaporation quantity detection apparatus equipped with the humidity sensor, took note of an attenuation portion of saw-tooth responses appearing for each blink in the tear evaporation profiles, and found that if this attenuation portion is approximated by an exponential function, the initial variation value and the attenuation ratio of this exponential function will have good correlation with the tear secretion quantity obtained by a Schirmer test and, therefore, the tear secretion quantity can be evaluated by the initial variation value and the attenuation ratio. This finding led to the creation of the first invention.

Thus, the first invention provides a tear secretion quantity examination system comprising a moisture evaporation quantity detection unit for detecting the moisture evaporation quantity from a subject's eye with a humidity sensor and operation means for computing the evaluation parameters of the tear secretion quantity based on a detection signal of the moisture evaporation quantity detection unit, wherein the operation means approximates the attenuation portion of saw-tooth responses appearing for each blink in a tear evaporation profile in which the detection value f(t) obtained with the humidity sensor is plotted against the time t, by the exponential function (1)

$$f(t)=Ae^{-kt}+B \qquad (1)$$

where A is an initial variation value, k is an attenuation ratio, and A, k, and B are respectively constants, and computes the initial variation value A and the attenuation ratio k as the evaluation parameters.

Further, the first invention also provides a tear secretion quantity evaluation method comprising the steps of obtaining a tear evaporation profile by plotting against the time t the detection value f(t) obtained while the subject blinks with the prescribed intervals, by using the humidity sensor of the above-described tear secretion quantity examination system, computing the initial variation value A and the attenuation ratio k by approximating the attenuation portion of saw-tooth responses appearing for each blink in the tear evaporation profile by the exponential function (1)

$$f(t)=Ae^{-kt}+B \qquad (1)$$

where A is an initial variation value, k is an attenuation ratio, and A, k, and B are respectively constants, and evaluating the tear secretion quantity based on the calculated initial variation value A and the attenuation ratio k.

The inventors have also discovered that tear evaporation profiles obtained by plotting the detection signal of the moisture evaporation quantity from the subject's eye against the time differ between a state prior to administration into the subject's eye and a state after administration and that the difference between the tear evaporation profiles obtained before and after administration differs significantly between a healthy person and a dry-eye patient, in particular, that the difference between the detection values of the tear evaporation profiles obtained before and after administration or the time variation ratio of the detection values immediately after the administration differ significantly, more specifically, that there is a large difference between the detection values of the tear evaporation profiles obtained before and immediately after administration or that the decrease ratio of the detection value immediately after administration is large. Furthermore, the inventors noticed that this trend has good correlation with the tear secretion quantity obtained by the Schirmer test, that is, that the tear secretion quantity can be evaluated by the difference between the detection values of the tear evaporation profiles obtained before and after administration or by the time variation ratio of the detection value immediately after administration. This finding led to the creation of the second invention.

Therefore, the second invention provides a tear secretion quantity examination system comprising a moisture evaporation quantity detection unit for detecting the moisture evaporation quantity from the subject's eye and operation means for computing the evaluation parameters of the tear secretion quantity based on the detection signal of the moisture evaporation quantity detection unit, wherein the operation means computes as the evaluation parameters the parameters representing the difference between a state prior to administration and a state after administration in the case in which an artificial tear fluid is dropped in the subject's eye, with respect to a tear evaporation profile in which the detection value obtained with the moisture evaporation quantity detection unit is plotted against the time.

In particular, in this tear secretion quantity examination system, a mode is provided in which operation means computes the difference between the detection values obtained before and immediately after administration and or the time variation ratio of the detection values immediately after administration in the case in which an artificial tear fluid is dropped in the subject's eye, with respect to a tear evaporation profile in which the detection value obtained with the moisture evaporation quantity detection unit is plotted against the time.

Further, the second invention provides a tear secretion quantity evaluation method comprising the steps of detecting the moisture evaporation quantity from the subject's eye before and after administration in the case in which an artificial tear fluid is dropped in the subject's eye, by using the moisture evaporation quantity detection unit of the above-described tear secretion quantity examination system, finding with the operation unit a tear evaporation profile in which the detection value is plotted against the time, and computing the parameters representing the difference between a state prior to administration and a state after the administration in the case in which an artificial tear fluid is dropped in the subject's eye, with respect to this profile.

DESCRIPTION OF THE PREFERRED EMBODIMENTS

The first invention will be initially described hereinbelow with reference to the appended drawings. In the figures, identical reference symbols represent identical or similar structural elements.

Figure 1:
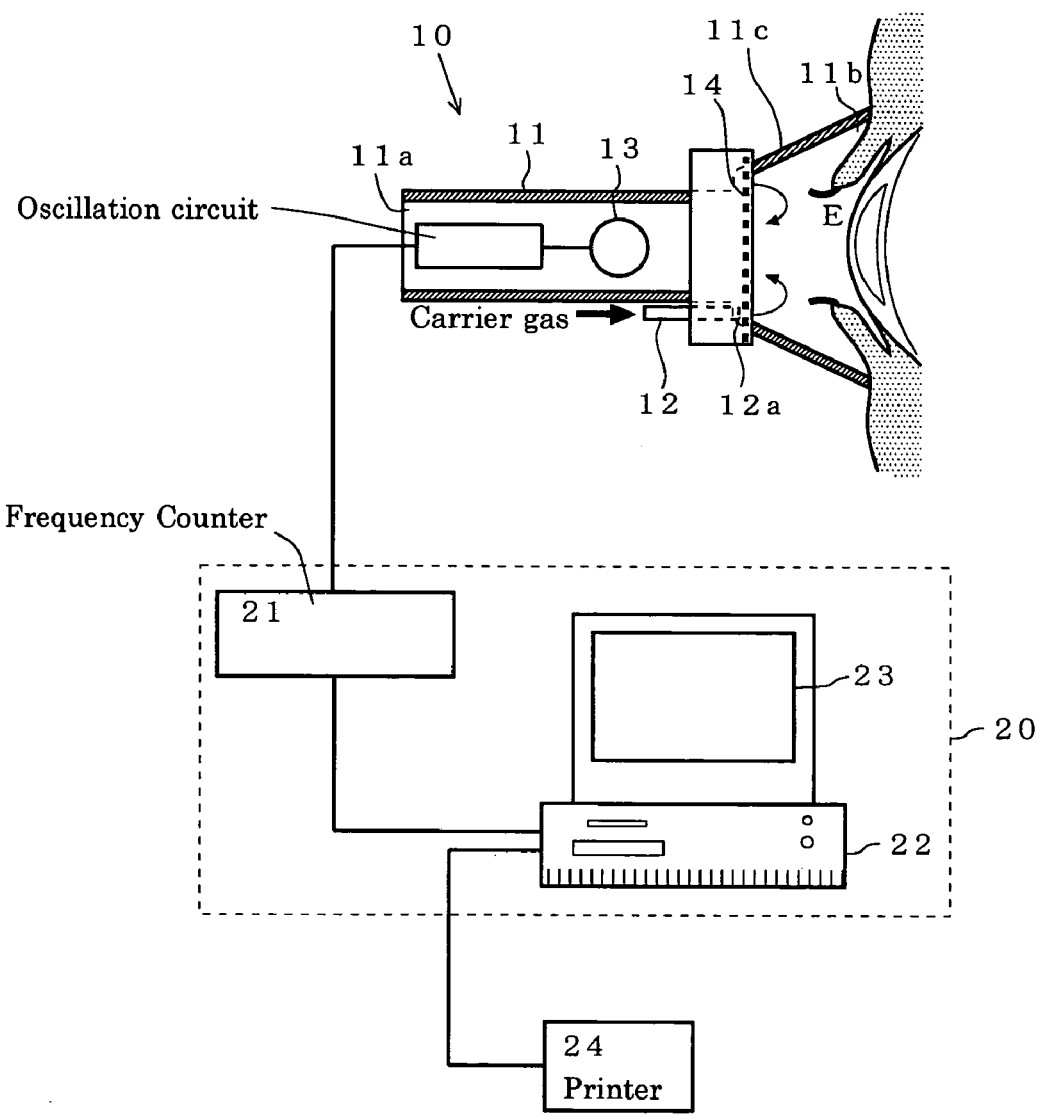
FIG. 1 is a schematic view of the tear secretion quantity examination system of the first and second invention.

FIG. 1 is a schematic view of an embodiment of a tear secretion quantity examination system 1 of the first invention. The tear secretion quantity examination system 1 is composed of a moisture evaporation quantity detection unit 10 for detecting the moisture that evaporated from the eye ball by a ventilated capsule method and operation means 20 for computing the evaluation parameters of tear secretion quantity based on the detection signal. A display 23 and a printer 24 are connected to the operation means 20.

The moisture evaporation quantity detection unit 10 comprises a tubular body 11 pressed against the eye E when the tear secretion quantity is examined, a gas introducing channel 12 for introducing a carrier gas into the tubular body 11, and a humidity sensor 13 provided inside the tubular body 11.

The tubular body 11 comprises open portions 11a, 11b at the lower and upper ends thereof. The lower open portion 11b has a size sufficient to surround the eye E. No specific limitation is placed on the shape of the tubular body 11, provided that it fits the shape of the face around the eye E. The tubular body 11 may be composed of a plurality of components. For example, the lower portion 11c of the tubular body may be formed by using swimming goggles or the like, so that the lower open portion 11b of the tubular body fits the shape of the face around the eye E.

During examination, the gas introducing channel 12 supplies a carrier gas with a constant moisture content through the tubular body 11 to the vicinity of eye E surface, preferably so as to avoid direct ejection of the carrier gas onto the eye E. Accordingly, a gas cylinder is connected to the front stage of the gas introducing channel 12, if necessary, via a gas drier.

No specific limitation is placed on the carrier gas used herein, provided that it produces no adverse effect on the eye. For example, dry air or dry nitrogen can be used.

The humidity sensor 13 is provided closer to the upper open portion 11a of the tubular body 11 than the open portion 12a of the gas introducing channel 12. A sensor of a resistor type or a capacitance type may be provided as the humidity sensor 13, but from the standpoint of increasing the measurement accuracy, a humidity sensor with a quarts oscillator is preferred.

Further, a shutter 14 for opening and closing the lower portion 11c is provided in the lower portion 11c of the tubular body 11 in a location at a certain distance from the lower open portion 11b.

In addition, an eye surrounding attachment comprising a shutter that can be opened and closed and a nozzle mechanism, as in a moisture evaporation quantity measurement device described in Japanese Patent Application Laid-open No. 2001-46339 may be provided in the lower portion 11c of the tubular body of the moisture evaporation quantity detection unit 10.

On the other hand, the operation unit 20 comprises a frequency counter 21 for receiving the detection signal produced by the humidity sensor 13 with a quartz oscillator and measuring the frequency of this signal and a personal computer 22. The personal computer 22 incorporates an operation program for creating a tear evaporation profile in which the value f(t) measured by the frequency counter 21 is plotted against the time t, and an operation program for approximating the attenuation portion of a saw-tooth response appearing for each blink in this tear evaporation profile by the exponential function (1)

$$f(t)=Ae^{-kt}+B \quad (1)$$

where A is an initial variation value, k is an attenuation ratio, A, k, and B are respectively constants, and computing the initial variation value A and attenuation ratio k by a least square method and outputting the results. Commercial products can be used as those operation programs.

The operation results obtained with the personal computer 22 are appropriately outputted, whenever required, to the display 23 and printer 24.

The tear secretion quantity examination system 1 is used in the manner as follows when the tear secretion quantity in the subject's eye E is examined.

First, the lower open portion 11b of the tubular body 11 is fit so as to surround the subject's eye E in a state in which the shutter 14 is closed, the carrier gas with a constant moisture content is supplied through the tubular body 11 from the gas introducing channel 12, and the excess gas is released from the upper open portion 11a. The detection of humidity is then started with the humidity sensor 13. Then, the shutter 14 is actuated and the lower open portion 11b of the tubular body 11 is opened. At this time, the subject's eye E is closed and the gas is continuously supplied into the tubular body 11. Once the detection value obtained with the humidity sensor 13 becomes constant, the subject is asked to blink at the prescribed intervals (for example, at intervals of 1 to 30 seconds).

Figure 2:
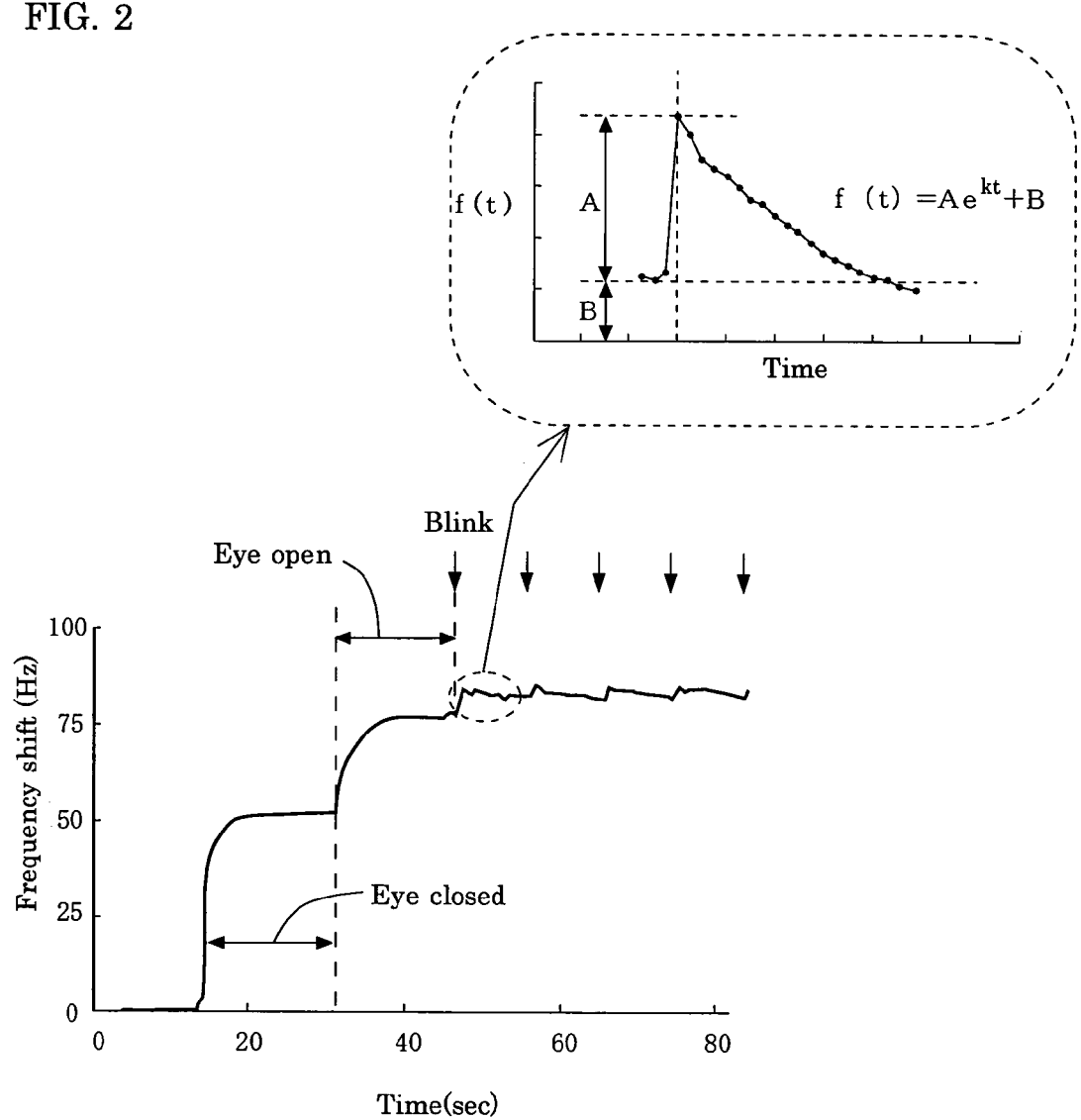
FIG. 2 is an explanatory drawing of a tear evaporation profile.

The personal computer 22 creates a tear evaporation profile shown in FIG. 2, from the detection values of humidity that were thus obtained, approximates the attenuation portion (portion surrounded by a broken line in the figure) of a saw-tooth response appearing for each blink in this tear evaporation profile by the exponential function (1)

$$f(t)=Ae^{-kt}+B \quad (1)$$

where A is an initial variation value, k is an attenuation ratio, A, k, and B are respectively constants, and computes the initial variation value A and attenuation ratio k by a least square method and outputs the results obtained to the display 23.

According to the information known to the inventors, the initial variation value A and attenuation ratio k have the following meaning. Thus, the smaller are the numerical values thereof, the smaller is the tear secretion quantity, in other words, the smaller is the variation of water vapor pressure on the eye surface caused by blinking. This trend demonstrates good correlation with the tear secretion quantity determined by a Schirmer test. Therefore, the initial variation value A and attenuation ratio k are suitable as evaluation parameters for a tear secretion quantity. Furthermore, with this system, the initial variation value A and attenuation ratio k for a dry-eye patient will be less than those for a healthy person, but this apparently corresponds to the fact that the absolute amount of a tear layer in the dry-eye patient is less than that in a healthy person.

When the system 1 of the first invention is used for evaluating the tear secretion quantity, first, a plurality of healthy people with a normal tear secretion quantity and a plurality of dry-eye patients with a small tear secretion quantity are selected as subjects and the initial variation value A and attenuation ratio k are found for the subjects. On the other hand, the dry-eye degree in ATD of each subject is classified into several stages by a Schirmer test, diagnostics, or the like, and converted into numerical values to find a dry-eye degree. For example, the numerical value of dry-eye degree in the section which is considered to correspond to a healthy state based on the Schirmer test, diagnostics, or the like, is assumed to be 0, and the numerical value of the dry-eye degree increases for the sections with a high intensity of dry-eye conditions. Data establishing the correspondence between the dry-eye degree thus found and the initial variation value A and attenuation ratio k are accumulated and the accumulated data are stored in the personal computer 22 itself of in an external hard disk connected to the personal computer 22 with a LAN or the like. The personal computer 22 makes it possible to refer to those accumulated data at any time. Furthermore, it is preferred that the personal computer 22 can compute the dry-eye degree of the subjects from the initial variation value A and attenuation ratio k based on the accumulated data.

As a result, the dry-eye degree of the subjects can be evaluated very easily and the subjects with a high dry-eye degree can be treated accordingly.

The moisture evaporation quantity detection unit used in accordance with the first invention is not limited to the above-described unit based on a ventilated capsule method. For example, a unit based on a sealed capsule method or an evaporimeter can be also used by mounting an attachment which is brought into tight contact with the skin around the eye.

The second invention will be described hereinbelow with reference to the appended drawings. In the figures, identical reference symbols represent identical or similar structural elements.

FIG. 1 is not only a schematic view of an embodiment of a tear secretion quantity examination system 1 of the first invention, but also a schematic view of an embodiment of a tear secretion quantity examination system 1 of the second invention. The tear secretion quantity examination system 1 is composed of a moisture evaporation quantity detection unit 10 for detecting the water that evaporated from the eye ball in a ventilated capsule method and operation means 20 for computing the evaluation parameters of tear secretion quantity based on the detection signal. A display 23 and a printer 24 are connected to the operation means 20.

The moisture evaporation quantity detection unit 10 comprises a tubular body 11 pressed against the eye when the tear secretion quantity is examined, a gas introducing channel 12 for introducing a carrier gas into the tubular body 11, and a humidity sensor 13 provided inside the tubular body 11.

The tubular body 11 comprises open portions 11a, 11b at the lower and upper ends thereof. The lower open portion 11b has a size sufficient to surround the eye E. No specific limitation is placed on the shape of the tubular body 11, provided that it fits the shape of the face around the eye E. The tubular body 11 may be composed of a plurality of components. For example, the lower portion 11c of the tubular body may be formed by using swimming goggles or the like, so that the lower open portion 11b of the tubular body fits the shape of the face around the eye E.

During examination, the gas introducing channel 12 supplies a carrier gas with a constant moisture content through the tubular body 11 to the vicinity of eye E surface, preferably so as to avoid direct ejection of the carrier gas onto the eye E. Therefore, a gas cylinder is connected to the front stage of the gas introducing channel 12, if necessary, via a gas drier.

No specific limitation is placed on the carrier gas used herein, provided that it produces no adverse effect on the eye. For example, dry air or dry nitrogen can be used.

The humidity sensor 13 is provided closer to the upper open portion 11a of the tubular body 11 than the open portion 12a of the gas introducing channel 12. A sensor of a resistor type or a capacitance type may be provided as the humidity sensor 13, but from the standpoint of increasing the measurement accuracy, a humidity sensor with a quarts oscillator is preferred.

Further, a shutter 14 for opening and closing the lower portion 11c is provided in the lower portion 11c of the tubular body 11 in a location at a certain distance from the lower open portion 11b.

In addition, an eye surrounding attachment comprising a shutter that can be opened and closed and a nozzle mechanism, as in a moisture evaporation quantity measurement unit described in Japanese Patent Application Laid-open No. 2001-46339 may be provided in the lower portion 11c of the tubular body of the moisture evaporation quantity detection unit 10.

The operation unit 20 comprises a frequency counter 21 for receiving the detection signal produced by the humidity sensor 13 with a quartz oscillator and measuring the frequency of this signal and a personal computer 22. The personal computer 22 incorporates an operation program for creating a tear evaporation profile in which the value f(t) measured by the frequency counter 21 is plotted against the time t, and an operation program for computing the difference in the evaporation quantity of tears between any two points in time and the time variation ratio of the evaporated quantity of tears at any point in time. Commercial products can be used as those operation programs.

The operation results obtained with the personal computer 22 are appropriately outputted, whenever required, to the display 23 and printer 24.

The tear secretion quantity examination system 1 is used in the manner as follows when the tear secretion quantity or retention quantity in the subject's eye E is examined.

First, in a state in which the shutter 14 is closed, the lower open portion 11b of the tubular body 11 is applied to the face so as to surround the subject's eye E, a carrier gas with a constant moisture content is supplied from the gas introducing channel 12 into the tubular body 11, and the excess gas is discharged from the open portion 11a in the upper open portion 11a. Humidity detection is then started with the humidity sensor 13, and a detection value ($Y_{base}$) serving as a reference is obtained. The shutter 14 is then actuated and the lower open portion 11b of the tubular body 11 is opened. At this time, the supply of gas into the tubular body 11 is continued and the subject's eye E is either in the closed state or open state (free blinking state).

Figure 6A:
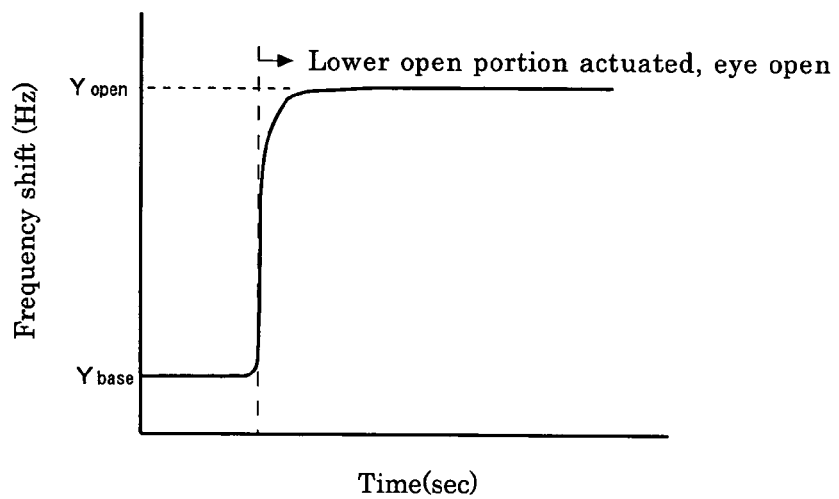
FIGS. 6A and 6B are explanatory drawings of tear evaporation profiles.
Figure 6B:
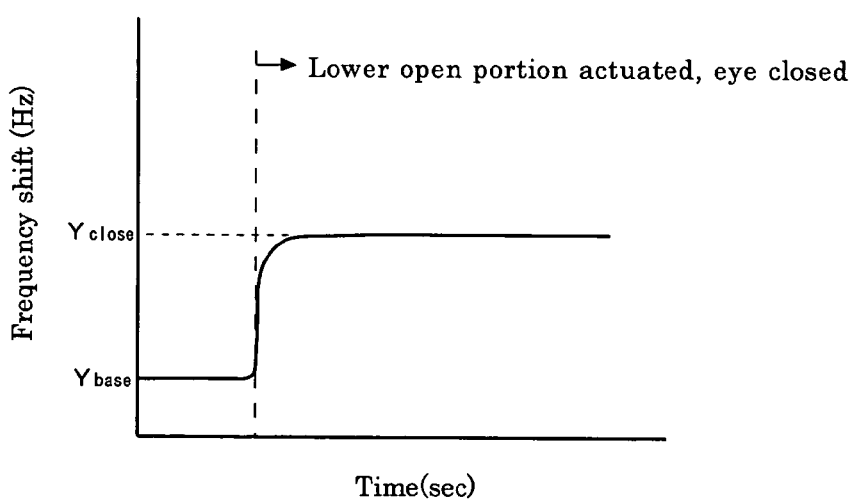

The personal computer 22 creates a tear evaporation profile in which the detection value of humidity thus obtained is plotted against the time and stores the detection values in this tear evaporation profile. Then, the difference between the value ($Y_{open}-Y_{base}$) obtained by subtracting the reference value $Y_{base}$ from the detection value $Y_{open}$ obtained when the eye was open, as shown in FIG. 6A, and the value ($Y_{close}-Y_{base}$) obtained by subtracting the reference value $Y_{base}$ from the detection value $Y_{close}$ obtained when the eye was closed, as shown in FIG. 6B, is considered as the detection value YS of tear evaporation quantity.

An artificial tear fluid is then dropped in an amount of 1–100 µL, preferably 5–10 µL, into the subject's eye, the tear evaporation profile is obtained immediately after administration in the same manner as described above, and the detection values thereof $Y_o$ are stored. Furthermore, the tear evaporation profile is obtained in the same manner after a time T has elapsed after administration (for example, 5 minutes and 10 minutes after administration) and the detection values $Y_T$ thereof are stored. The difference $\Delta Y_{o-s}$ between the detection value $Y_o$ immediately after administration and the detection value $Y_s$ prior to administration and the time variation ratio $Z_o$ of the detection value immediately after administration are computed and stored.

The inventors know that in healthy people, the detection value in the tear evaporation profile is practically not changed by administration, whereas in the dry-eye patients the detection value increases immediately after administration and then returns to the level attained prior to administration in about 10 minutes. Therefore, in a dry-eye patient, the difference $\Delta Y_{o-s}$ between the detection values obtained before and immediately after administration is large and the time variation ratio $Z_o$ immediately after administration assumes a large negative value. This is apparently because in the case of dry-eye patients, the tear secretion quantity is normally small and the tear evaporation quantity is large, which results in the absence of a sufficient tear layer on the eye surface. However, because due to administration the tear retention quantity on the eye surface becomes equal to or larger than that in healthy people, the tear evaporation quantity increases with time and, therefore, the difference $\Delta Y_{o-s}$ between the detection values increases. Furthermore, in the case of dry-eye patients, because the tear retention quantity increased by administration cannot be maintained, the tear evaporation quantity rapidly decreases with time immediately after administration and the time variation ratio $Z_o$ of the detection values immediately after administration assumes a large negative value. By contrast, because in the healthy people, a tear layer is apparently always formed on the eye surface, the tear evaporation quantity from the eye apparently does not change, regardless of administration.

Therefore, the tear secretion quantity and retention quantity can be evaluated by considering the difference $\Delta Y_{o-s}$ between the detection values before and immediately after administration and the time variation ratio $Z_o$ of detection values immediately after administration.

When the system 1 of the second invention is used for evaluating the tear secretion quantity, first, a plurality of healthy people with a normal tear secretion quantity and a plurality of dry-eye patients with a small tear secretion quantity are selected as test subjects, and the difference $\Delta Y_{o-s}$ between the detection values obtained before and immediately after administration and the time variation ratio $Z_o$ of detection values immediately after administration are found for each test subject. On the other hand, the dry-eye degree in ATD of each subject is classified into several stages by the Schirmer test and diagnostics and converted into numerical values to find a dry-eye degree. For example, in the section which is considered to correspond to a healthy state based on the Schirmer test or diagnostics, the numerical value of the dry-eye degree is considered to be 0, and the numerical value of the dry-eye degree increases for the sections with a high intensity of dry-eye conditions. Data establishing the correspondence between the dry-eye degree thus found and the aforesaid difference $\Delta Y_{o-s}$ between the detection values and time variation ratio $Z_o$ of detection values are accumulated and the accumulated data are stored in the personal computer 22 itself or in an external hard disk or the like which is connected to the personal computer 22 with a LAN or the like. Further, the personal computer 22 refers to the accumulated data whenever required. Further, it is preferred that based on the accumulated data, the personal computer 22 can compute the dry-eye degree of the subjects from the aforesaid difference $\Delta Y_{o-s}$ between the detection values obtained before and after administration and time variation ratio $Z_o$ of the detection values obtained for the subjects. As a result, the dry-eye degree of the subjects can be evaluated extremely easily.

The explanation hereinabove was provided with respect to the case in which operation means computed the difference $\Delta Y_{o-s}$ between the detection values obtained before and after administration and the time variation ratio $Z_o$ of the detection values immediately after administration as evaluation parameters for the tear secretion quantity or retention quantity. However, in the system in accordance with the present invention, other parameters demonstrating different values before and after administration may be computed with respect to the tear evaporation profile and those parameters may be used as evaluation parameters for the tear secretion quantity or retention quantity.

Furthermore, the moisture evaporation quantity detection unit used in accordance with the second invention is not limited to the above-described unit based on a ventilated capsule method. For example, a unit based on a sealed capsule method or an evaporimeter can be used upon installing an attachment allowing it to be brought into tight contact with the skin around the eye.

EXAMPLES

Example 1

One healthy person and two dry-eye patients were selected as subjects and the initial variation value A and attenuation ratio k were found for each subject with the system shown in FIG. 1. In this case, air with a relative humidity of 10% was used at a flow rate of 150 mL/min as a carrier gas in the moisture evaporation detection unit 10. Further, the blinking interval during detection of the tear secretion quantity was set to 5 or 10 seconds.

Figure 3:
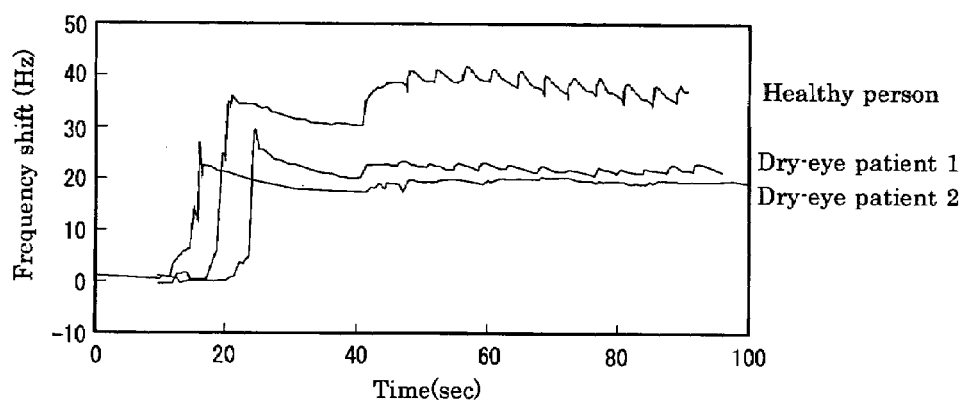
FIG. 3 is a tear evaporation profile of Example 1.

The obtained tear evaporation profile (blinking interval 5 seconds) is shown in FIG. 3. FIG. 3 clearly demonstrates that the shapes of the saw-tooth responses generated by blinking differ between the subjects.

Figure 4:
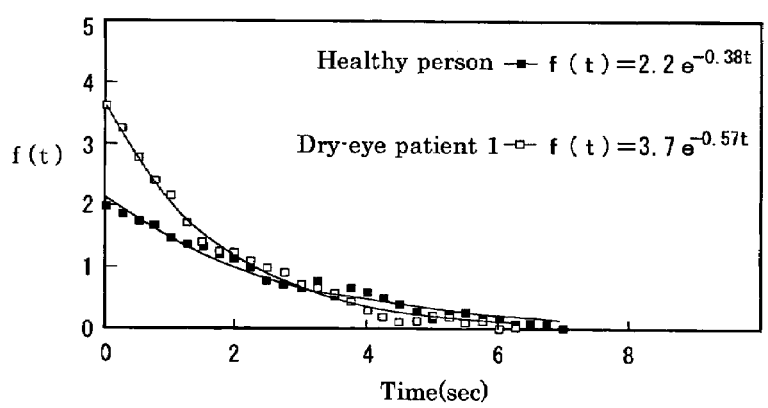
FIG. 4 shows the analysis results relating to a saw-tooth-like attenuation portion in the tear evaporation profile of Example 1.

Furthermore, the results obtained in analyzing the attenuation portion of the saw-tooth response appearing for each blink in the tear evaporation profile (blinking interval 10 seconds) is shown in FIG. 4.

On the other hand, a Schirmer test was conducted on the subjects. The initial variation value A and attenuation ratio k of the tear evaporation profiles and the Schirmer test values are shown in Table 1.

TABLE 1

|  | Initial variation value A | Attenuation ratio k | Schirmer test value |
|---|---|---|---|
| Healthy person | 3.7 Hz | 0.57 | 35 mm |
| Dry-eye patient 1 | 2.2 Hz | 0.38 | 15 mm |
| Dry-eye patient 2 | 0 Hz | 0 | 4 mm |

Table 1 demonstrates that the numerical values of the initial variation value A and attenuation ratio k are lower for the dry-eye patients, similarly to the Schirmer test values.

Example 2

The initial variation value A and attenuation ratio k of the tear evaporation profile and the Schirmer test values were found for six dry-eye patients and six healthy people in the same manner as in Working Example 1, except that the blinking interval was set to 10 seconds.

The following results were obtained for the average values ± standard deviations of the initial variation value A and attenuation ratio k. For the dry-eye patients: initial variation value A=1.82±0.33 [Hz], attenuation ratio k=0.335±0.106. For the healthy people: initial variation value A=4.17±2.26 [Hz], attenuation ratio k=0.489±0.111.

It is apparent that the values of the initial variation value A and attenuation ratio k obtained for the dry-eye patients tend to be lower than those obtained for the healthy people (it is significant that for the attenuation ratio k, $p<0.05$).

Furthermore, the initial variation value A and attenuation ratio k obtained for six dry-eye patients were plotted against the Schirmer test values. The results are shown in FIG. 5.

Figure 5:
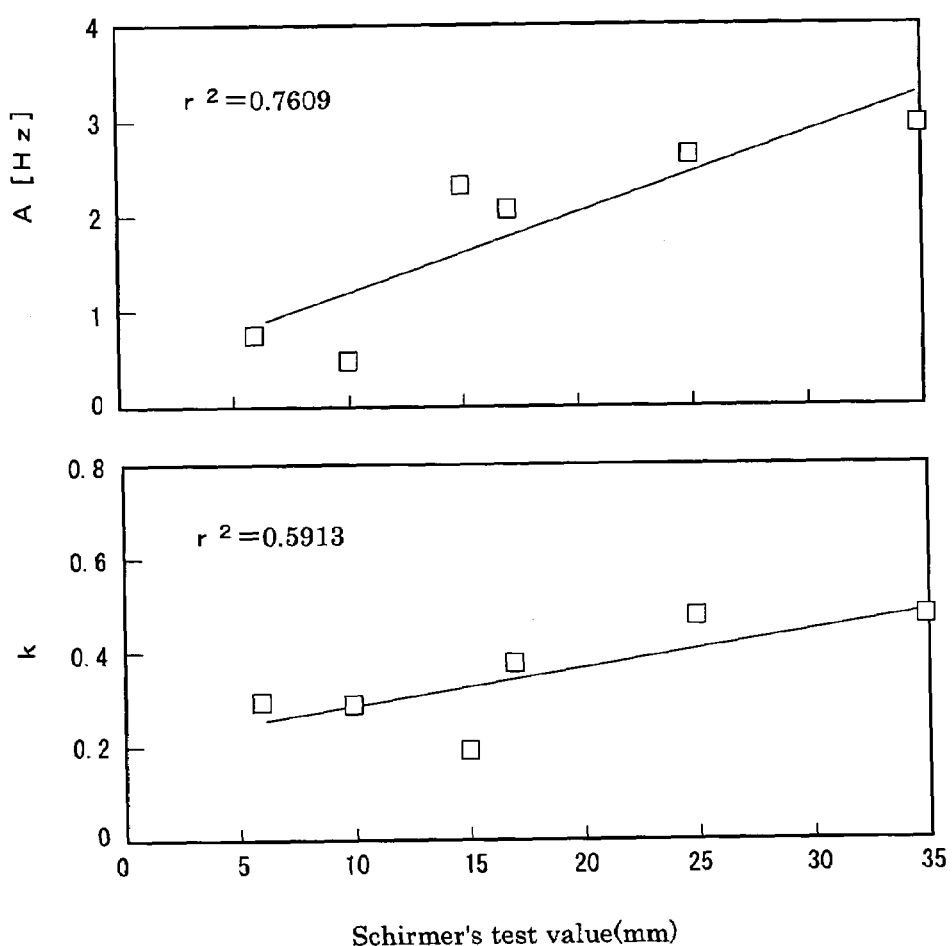
FIG. 5 illustrates a relation between the initial variation value A or attenuation ratio k and the Schirmer test value.

FIG. 5 clearly demonstrates that the initial variation value A and attenuation ratio k have correlation with the Schirmer test values.

With the system of the first invention, the initial variation value A and attenuation ratio k can be computed from the tear evaporation profile and used as the evaporation parameters for the tear secretion quantity. Therefore, a dry-eye evaluation system replacing the Schirmer test is obtained.

Example 3

One healthy person and one dry-eye patient were selected as subjects and the tear evaporation profiles were found for each subject before and after administration 7 μL of an artificial tear fluid by using the system shown in FIG. 1. In this case, air with a relative humidity of 10% RH was used at a flow rate of 150 mL/min as a carrier gas in the moisture evaporation detection unit 10. Further, the blinking interval during detection of the tear secretion quantity was freely selected.

Figure 7:
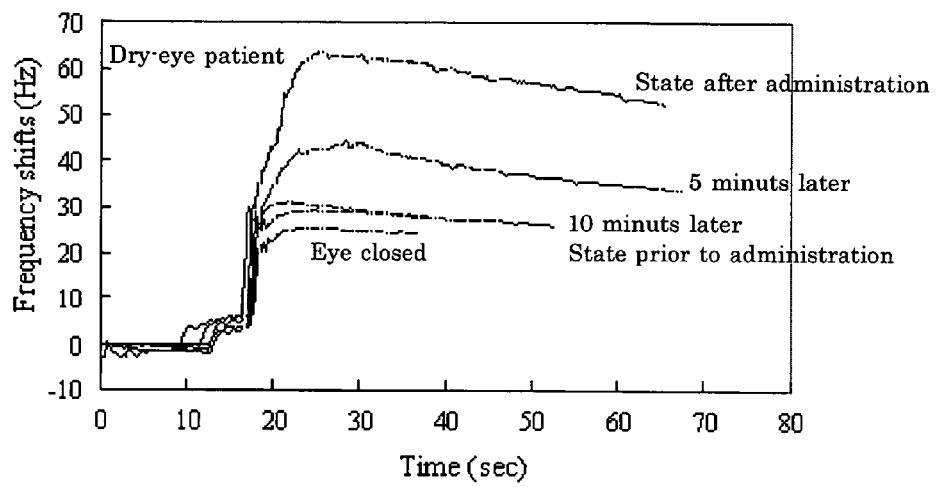
FIG. 7 shows tear evaporation profiles before and after administration to a dry-eye patient.
Figure 8:
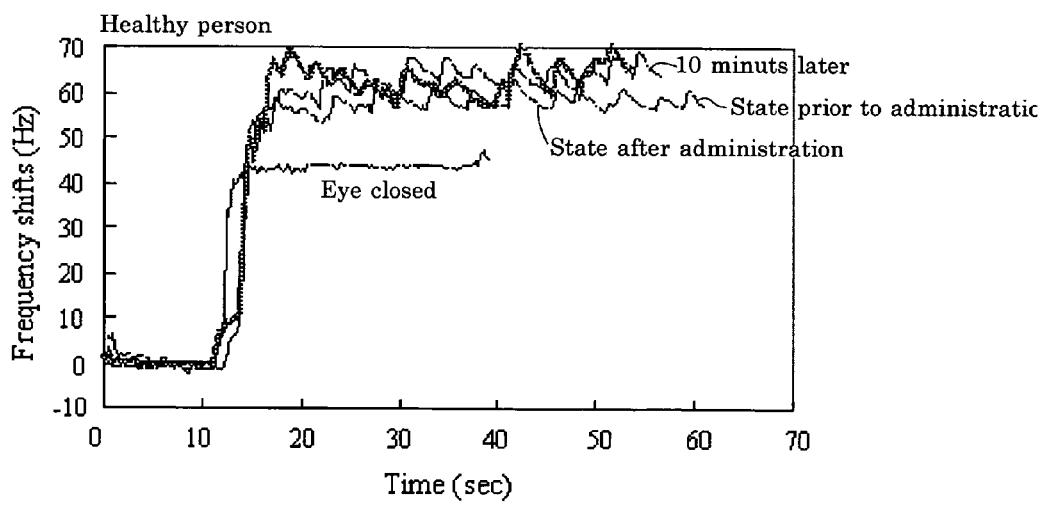
FIG. 8 shows tear evaporation profiles before and after administration to a healthy person.

The obtained tear evaporation profiles are shown in FIGS. 7 and 8. From the results shown in FIGS. 7 and 8, the tear evaporation quantity per unit time related to the interval after administration was computed by the following formula (2) by using the calibration curve of frequency changes vs. humidity changes that was found in advance.

$$J=(1/A)\cdot(\Delta F/(k\cdot 100))\cdot \rho \cdot V \qquad (2)$$

where A: measurement surface area ($cm^2$),
ΔF: frequency shift (Hz),
k: slope of calibration curve (sensor constant) (Hz),
ρ: moisture content in air with a relative humidity of 100% RH ($g/cm^3$),
V: flow rate of carrier gas ($cm^3/sec$).

Figure 9:
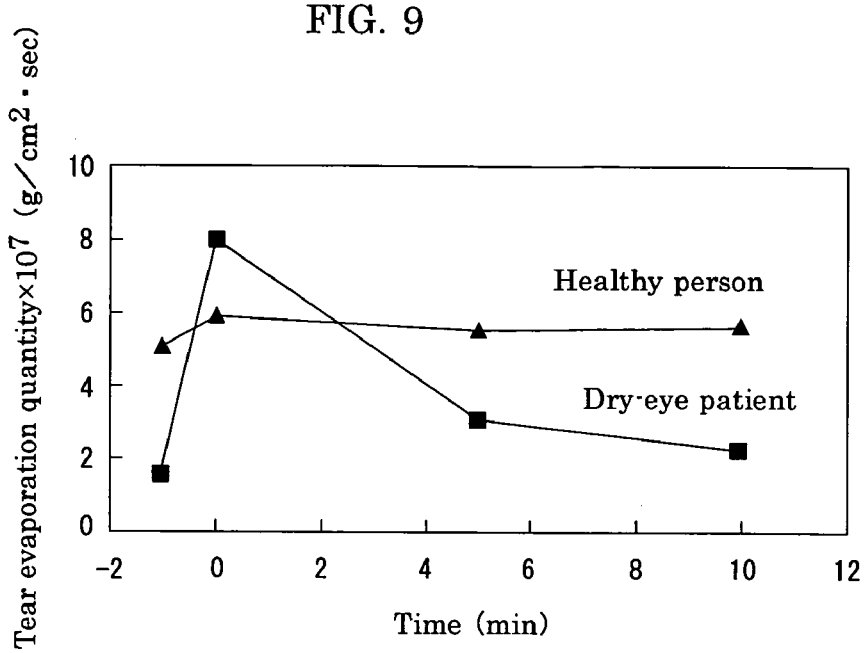
FIG. 9 illustrates the relation between the tear evaporation quantity and time after administration.

The results are shown in FIG. 9. Furthermore, from the results shown in FIG. 9, the difference ΔY in the tear evaporation quantity per unit time obtained before administration and immediately after administration and the time variation ratio Z of tear evaporation quantity obtained immediately after administration were computed for each subject. The Schirmer test was also conducted for each subject. The results obtained are shown in Table 2.

TABLE 2

|  | Difference in tear evaporation quantity ΔY × $10^7$ (g/$cm^2$ · sec) | Time variation ratio of tear evaporation quantity Z × $10^7$ (g/$cm^2$ · sec) | Schirmer test value |
|---|---|---|---|
| Healthy person | 0.8 | −0.0017 | 35 mm |
| Dry-eye patient | 6.4 | −0.017 | 6 mm |

FIGS. 7 through 9 and Table 2 clearly demonstrate that in the dry-eye patients the tear evaporation quantity increased immediately after administration, but after 10 minutes returned to the level attained before administration. Therefore, the difference between the tear evaporation quantities obtained before administration and immediately after administration was large and the time variation ratio of the tear evaporation quantity obtained immediately after administration assumed a large negative value. By contrast, in the healthy person, practically no changes in the tear evaporation quantity caused by administration were observed.

Therefore, it is possible to evaluate as to whether the person has a dry eye condition from the difference between the tear evaporation quantities obtained before administration and immediately after administration and the time variation ratio of tear evaporation quantity obtained immediately after administration. Furthermore, it is clear that this evaluation matches that based on the Schirmer test values.

Example 4

The difference between the tear evaporation quantities obtained before administration and immediately after administration was found from the tear evaporation profile in the same manner as in Working Example 3 with respect to nine dry-eye patients and two healthy people. Furthermore, the Schirmer test values were found and the difference between the tear evaporation quantities obtained before administration and immediately after administration was plotted against the Schirmer test values. The results are shown in FIG. 10.

Figure 10:
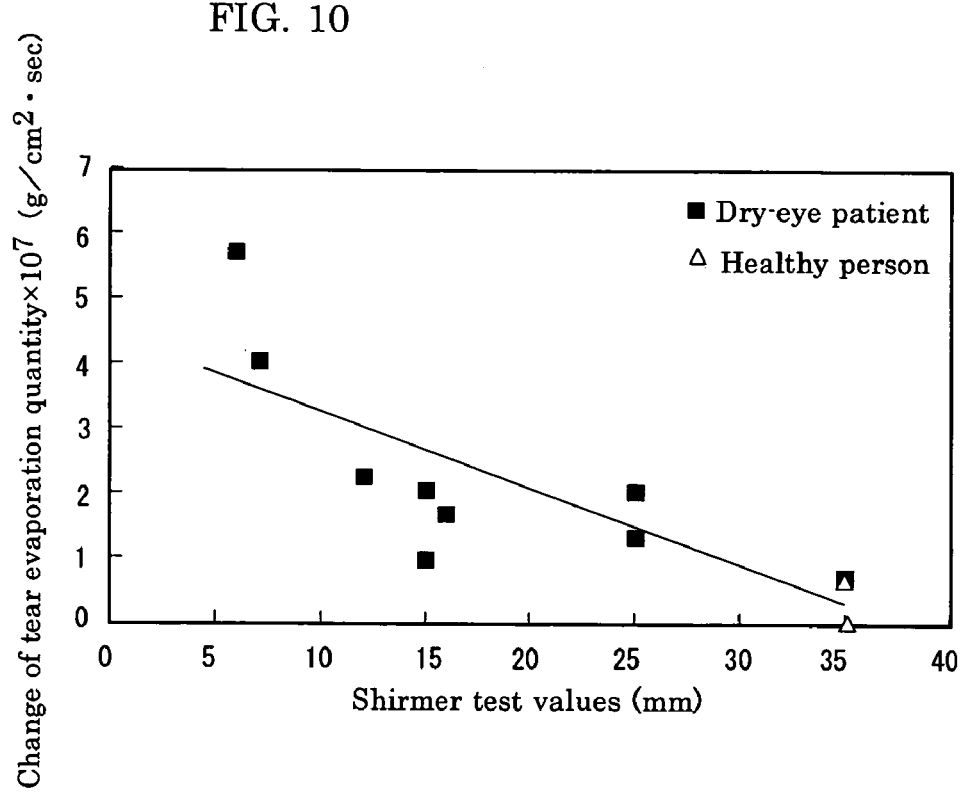
FIG. 10 illustrates the dependence of the difference between the tear evaporation quantity before and immediately after administration on the Schirmer test value.

FIG. 10 clearly demonstrates that the difference between the tear evaporation quantities obtained before administration and immediately after administration has correlation with the Schirmer test values.

With the system of the second invention, parameters representing the difference between the tear evaporation profiles obtained before and after administration of an artificial tear fluid are used as evaluation parameters for the tear secretion quantity. Therefore, the tear secretion quantity or retention quantity can be evaluated in an easy and non-invasive manner.

The entire disclosures of the specifications, claims, summaries, drawings and abstracts of Japanese Patent Applications No. 2003-032898 and No. 2003-032899, both filed on Feb. 10, 2003, are hereby incorporated by reference.

What is claimed is:

1. A tear secretion quantity examination system comprising: a moisture evaporation quantity detection unit for detecting the moisture evaporation quantity from a subject's eye with a humidity sensor; and operation means for computing evaluation parameters of the tear secretion quantity based on a detection signal of said moisture evaporation quantity detection unit, wherein
the operation means approximates the attenuation portion of saw-tooth responses appearing for each blink in a tear evaporation profile in which the detection value f(t) obtained with the humidity sensor is plotted against the time t, by the exponential function (1)

$$f(t)=Ae^{-kt}+B \qquad (1)$$

where A is an initial variation value, k is an attenuation ratio, and A, k, and B are respectively constants, and computes the initial variation value A and the attenuation ratio k as said evaluation parameters.

2. The tear secretion quantity examination system according to claim 1, wherein a plurality of healthy people with a normal tear secretion quantity and a plurality of dry-eye patients with a small tear secretion quantity are selected as subjects, the accumulated data establishing the correspondence between the initial variation value A calculated and the attenuation ratio k calculated for each subject and the dry-eye degree of each subject are referred to by the operation means, and the dry-eye degree of the subjects is calculated from the initial variation value A and the attenuation ratio k of said subjects, based on said accumulated data.

3. A tear secretion quantity evaluation method comprising the steps of:
obtaining a tear evaporation profile by plotting against the time t the detection values f(t) obtained while subjects blink with the prescribed intervals, by using the humidity sensor of the tear secretion quantity examination system according to claim 1,
computing the initial variation value A and the attenuation ratio k by approximating the attenuation portion of saw-tooth responses appearing for each blink in said tear evaporation profile by the exponential function (1)

$$f(t)=Ae^{-kt}+B \qquad (1)$$

where A is an initial variation value, k is an attenuation ratio, and A, k, and B are respectively constants; and
evaluating the tear secretion quantity based on the calculated initial variation value A and the calculated attenuation ratio k.

4. The tear secretion quantity evaluation method according to claim 3, wherein the initial variation value A and the attenuation ratio k are calculated for a plurality of healthy people with a normal tear secretion quantity and a plurality of dry-eye patients with a small tear secretion quantity as subjects, data establishing the correspondence between the initial variation value A calculated and the attenuation ratio k calculated for each subject and the dry-eye degree of each subject are accumulated, while the initial variation value A and the attenuation ratio k of the subjects are calculated, and the dry-eye degree of the subjects is calculated from the calculated initial variation value A and the calculated attenuation ratio k of the subjects, based on said accumulated data.

5. A tear secretion quantity examination system comprising: a moisture evaporation quantity detection unit for detecting the moisture evaporation quantity from a subject's eye and operation means for computing evaluation parameters of the tear secretion quantity based on a detection signal of said moisture evaporation quantity detection unit, wherein
said operation means computes, as said evaluation parameters, the parameters representing the difference between a state prior to administration and a state after the administration in the case in which an artificial tear fluid is dropped in the subject's eye, with respect to a tear evaporation profile in which a detection value obtained with the moisture evaporation quantity detection unit is plotted against the time.

6. A tear secretion quantity examination system, wherein operation device computes, as evaluation parameters, the difference between the detection values obtained before and immediately after administration or the time variation ratio of the detection values immediately after administration in the case in which an artificial tear fluid is dropped in the subject's eye, with respect to a tear evaporation profile in which a detection value obtained with the moisture evaporation quantity detection unit is plotted against the time.

7. The tear secretion quantity examination system according to claim 5, wherein the moisture evaporation quantity detection unit comprises: a tubular body comprising open portions at the lower and upper ends thereof, the lower open portion surrounding the eye; a gas introducing channel for introducing a carrier gas into the tubular body; and a humidity sensor provided inside the tubular body.

8. The tear secretion quantity evaluation system according to claim 5, wherein a plurality of healthy people with a normal tear secretion quantity and a plurality of dry-eye patients with a small tear secretion quantity are selected as subjects, and the operation means refers to accumulated data establishing the correspondence between the difference between the detection values obtained before and immediately after administration of said artificial tear fluid or the time variation ratio of the detection values immediately after administration for each subject and the dry-eye degree of each subject, and the dry-eye degree of the subjects is computed from the difference between the detection values obtained before and immediately after administration of said artificial tear fluid or the time variation ratio of the detection values immediately after administration to the subjects, based on said accumulated data.

9. A tear secretion quantity evaluation method comprising the steps of:

detecting the moisture evaporation quantity from a subject's eye before and after administration in the case in which an artificial tear fluid is dropped in the subject's eye, by using the moisture evaporation quantity detection unit of the tear secretion quantity examination system according to claim 1;

finding with the operation unit a tear evaporation profile in which the detected values are plotted against the time; and computing the parameters representing the difference between a state prior to administration and a state after the administration in the case in which an artificial tear fluid is dropped in the subject's eye, with respect to the profile.

* * * * *